United States Patent [19]

Brault et al.

[11] 3,969,669

[45] July 13, 1976

[54] METHOD AND APPARATUS FOR CONTINUOUSLY DETERMINING THE INTERNAL RESISTANCE OF AN ELECTROLYSIS CELL

[75] Inventors: Thierry Brault, St.-Michel-de-Maurienne; Jean-Claude Lacroix, Chambery, both of France

[73] Assignee: Aluminum Pechiney, Lyon, France

[22] Filed: May 7, 1975

[21] Appl. No.: 575,479

[30] Foreign Application Priority Data

June 5, 1974   France .............................. 74.19297

[52] U.S. Cl. ............................. 324/65 R; 324/30 R
[51] Int. Cl.² ....................................... G01R 27/02
[58] Field of Search ............. 324/65 R, 30 A, 30 B, 324/30 R

[56] References Cited
UNITED STATES PATENTS 3,355,661   11/1967   Nonaka ........................... 324/30 A
3,909,709   9/1975   Maxon .............................. 324/65 R Primary Examiner—Stanley T. Krawczewicz
Attorney, Agent, or Firm—McDougall, Hersh & Scott

[57] ABSTRACT

The invention relates to a method of continuously determining the internal resistance of an electrolysis cell and to an apparatus for carrying out this method. In the method according to the invention a weak alternating current (if) of frequency (f) is superimposed upon the electrolysis current, the active part (rf) of the impedance which the cell offers to this alternating current is measured, followed by extrapolation to the zero frequency of the function giving the active part (rf) of the impedance as a function of the frequency (f), (rf) thus inclining towards the internal resistance of the cell. The invention is applicable to any electrolysis cell and more particularly to cells for the igneous electrolysis of alumina.

12 Claims, 23 Drawing Figures

METHOD AND APPARATUS FOR CONTINUOUSLY DETERMINING THE INTERNAL RESISTANCE OF AN ELECTROLYSIS CELL

This invention relates to a method of continuously determining the internal resistance of an electrolysis cell, and to an apparatus for carrying out this method.

An electrolysis cell comprises a compartment containing an electrically conductive bath and two electrodes, an anode connected to the positive pole of a direct-current source and a cathode connected to the negative pole of that source. The current flows between these two electrodes and decomposes the electrolysis bath or one of its constituents into two components which appear at the anode and cathode, respectively. The electrochemical process uses a certain amount of energy which is reflected in a voltage drop known as the counterelectromotive force.

If
U is the voltage at the terminals of the electrodes,
R is the internal resistance of the electrolysis cell at the terminals of which the voltage U is tapped,
E is the counterelectromotive force of electrolysis,
I is the intensity of the electrical current flowing through the cell,
the following relation is obtained:

$$U = E + RI.$$

U.I is the total power supplied to the cell, E.I. is the power used by the electrolysis process, and $RI^2$ is the power dissipated into the internal resistance of the cell.

In the case of electrolysis cells used for the production of aluminum by the electrolysis of alumina dissolved in cryolite, this dissipated power enables the electrolysis bath to be kept at a temperature above its melting temperature, i.e., approximately 950° to 1000°C. In this case, the two electrodes are made of carbon, the cathode forming the base of the cell and the anode being made up of one or more blocks of carbon dipping into the bath. The alumina is decomposed into aluminium which is deposited in the form of a liquid layer onto the cathode, whilst the oxide ions are discharged at the surface of the anode which thus undergoes progressive combustion.

Disregarding outside intervention, there are two main causes for the variation in internal resistance, namely the increase in level of the so-called anodic plane, which limits the system of anodes facing the cathode as a result of the combination of the anodes, and the progressive depletion of alumina in the electrolysis bath. When the alumina content falls below a critical level, of the order of 1 to 3%, the anode is polarised, in other words the nature of the electrolytic process changes, modifying both the internal resistance and the counterelectromotive force to a considerable extent. Since a certain number of cells are mounted in series, the current I, which is regulated, hardly varies and the phenomenon is reflected in a significant increase in the voltage U at the terminals of the polarized cell.

It is therefore important to know the value of the internal resistance of an electrolysis cell so as to be able to regularise the electrolysis process.

It is known that this resistance can be calculated in accordance with the following formula:

$$R = \frac{U - E}{I}$$

U and I are easy to measure, whereas E is unknown. Accordingly, a constant mean value, such as 1.65 volts, is assumed for E. This is the so-called "pseudo-resistance" process currently used in electrolysis cells.

Recent work carried out with a view to improving present performance levels whilst, at the same time, ensuring automatic, stable operation has prompted a search for greater precision by determining both the internal resistance and the counterelectromotive force. German Patent Application 2,050,126 which was filed by Siemens AG on the 13th examination October, 1970 and published before examinnation on the 20th April, 1972, relates to a method of measuring the internal resistance of an electrolysis cell. The inventor defines the alternating-current reactance X of the cell and postulates that, for a small variation $\Delta 1$ in the level of the anodic plane, the variation $\Delta X$ of the reactance is proportional to $\Delta 1$:

$$1 = m\, \Delta X$$

where m is only governed by the construction of the cell.

He then postulates that the variation $\Delta R$ in the resistance of the cell, based on the unit length of the displacement of the anodic plane may be written as follows for low values of $\Delta 1$:

$$\frac{\Delta R}{\Delta 1} = a_{11} k_1 + C$$

where k1 is the concentration of alumina and $a_{11}$ and C are constants?

If, during the displacement $\Delta 1$, the reactance undergoes a variation of $\Delta X$ and the resistance a variation of $\Delta R$, then:

$$\frac{\Delta R}{m \Delta X} = a_{11} k_1 + C$$

so that $$k_1 = \frac{1}{a_{11}} \left( \frac{\Delta R}{m \Delta X} - C \right)$$

It is sufficient to make two variations in interpolar distance, each being made for a known alumina concentration $k_1$, in order to determine $a_{11}$ and C: it is then possible to determine the value of m for the given cell and, hence, to associate K1 with $\Delta R$ and $\Delta X$.

The author then postulates that R may be compared with the alternating-current resistance $R'$ of the cell at a very low frequency $f$.

In order to measure the impedance of the cell at the frequency $f$, he injects and alternating current of the same frequency into the cell and measures the voltage at the terminals of the cell and the intensity of the current flowing through it. He separates the direct-current component and the alternating-current component by filtration. The alternating-current components of the voltage and intensity are treated in four synchronous detectors so as to determine the real and imaginary parts of the voltage and intensity, the phase reference being taken from the generator supplying the alternating current injected. He then deduces R' which he assimilates with R and, from that value, the counter-electromotive force E. The information is digitalised and treated in real time by a computer.

The method described above is based on several hypotheses which are not confirmed by experience with industrial cells in particular. In the first place, the hypothesis on the alternating current resistance seeks to equate the behaviour of the cell with that of an assembly of passive elements. However, experience has shown that the real part of the impedance, i.e., the alternating current resistance, may disappear and become negative which necessitates the presence of active elements. The inventor also postulates that $\Delta 1 = m \Delta X$. This is only confirmed for extremely low variations of $\Delta 1$ and this approach can only have the significance of a series development confined to the linear term.

The present invention relates to a method of continuously determining the internal resistance of an electrolysis cell which obviates the disadvantages referred to above.

The invention also relates to an apparatus for carrying out this method.

In the method according to the invention, a weak alternating current if of frequency f is superimposed upon the direct current used for electrolysis, the active part rf of the impedance which the cell offers to this alternating current is determined, followed by extrapolation to the zero frequency of the function giving the active part rf of the impedance in dependence upon the frequency f, this active value thus tending towards the internal resistance r of the cell.

The apparatus according to the invention comprises a low-frequency generator comprising, on the one hand, a sinusoidal output connected to a current converter connected between two points on the bars feeding the cell on either side thereof, and superimposing a sinusoidal current if upon the direct current I flowing through the cell, and on the other hand a square signal output connected to a galvanically insulated reference amplifier, an inductive current-measuring probe if placed between the two above-mentioned points and, attacking a first synchronous detector whose reference input is connected to the output of the galvanically insulated reference amplifier, an amplifier/a.c. - d.c. separator whose inputs are connected to the poles of the cell and whose output, giving the alternating-current component uf of the voltage V at the poles of the cell, attacks a second synchronous detector whose reference input is also connected to the output of the galvanically insulated reference amplifier, and a dividing operator whose inputs are connected to the outputs $u_o$ and iof, respectively, of the synchronous detectors associated with uf and if.

Exemplary embodiments of the invention are described in the following with reference to the accompanying drawings, wherein.

In all these Figures, the same reference numerals have been used to denote identical components.

The method for continuously determining the internal resistance of an electrolysis cell comprises superimposing a weak alternating current upon the electrolysis current. The cell is regarded as an impedance of which the active part and reactive part are successively determined at a given frequency. The variations in the active part as a function of frequency are used for determining the direct-current resistance value R of the cell by extrapolation to the zero frequency. The d.c. voltage U at the terminals of the cell and the intensity I of the direct current flowing through it may then be measured and the counterelectromotive force of electrolysis E determined by:

$$E = U - RI$$

The value of R thus determined may be used as reference point for regulating the position of the anodic plane, for example by means of the arrangement described in French Patent No. 1,397,946 (application filed 29th March, 1965 in the name of PECHINEY, Compagnie de Produits Chimiques et Electrometallurgiques.).

The direct current of intensity I flowing through the cell then has superimposed upon it an alternating current of frequency f and intensity if, preferably of the order of $10^{-4}$ to $10^{-5}$ I. The total voltage V at the terminals of the cell is thus:

$$V = U + uf = E + RI + Z_f i_f$$

where uf is the a.c. voltage produced by the current if and Zf is the impedance of the cell at the frequency f.

V is measured and its d.c. component U is separated by filtration from its a.c. component uf. if Is simultaneously measured, for example by an induction method.

The component of uf, which is in phase with if, and the component which is in quadrature with if are then measured by means of a synchronous detector. From the result of these two measurements it is deduced that:

$$Zf = rf + jXf \qquad tg\phi f = \frac{Xf}{rf}$$

where rf and Xf are the components of Zf which are in phase and quadrature, respectively, with if, and φ is the phase angle of uf relative to if.

The real part rf of the impedance corresponds to the energy dissipated in the cell by the alternating current of frequency f, whilst only the energy dissipated by Joule effect corresponds to R. If the frequency f is inclined towards zero, rf inclines towards R. The curve giving rf as a function of the frequency f is then drawn, followed by extrapolation to the zero value of the variable so as to obtain $r(f=0) = R$.

In practice, the procedure is somewhat more complicated. The reference used is the low-frequency signal used to modulate the electrolysis current so as to obtain the superimposed current if, and uf and if are separately treated by synchronous detection, the results subsequently being divided to give rf.

Figure 1:
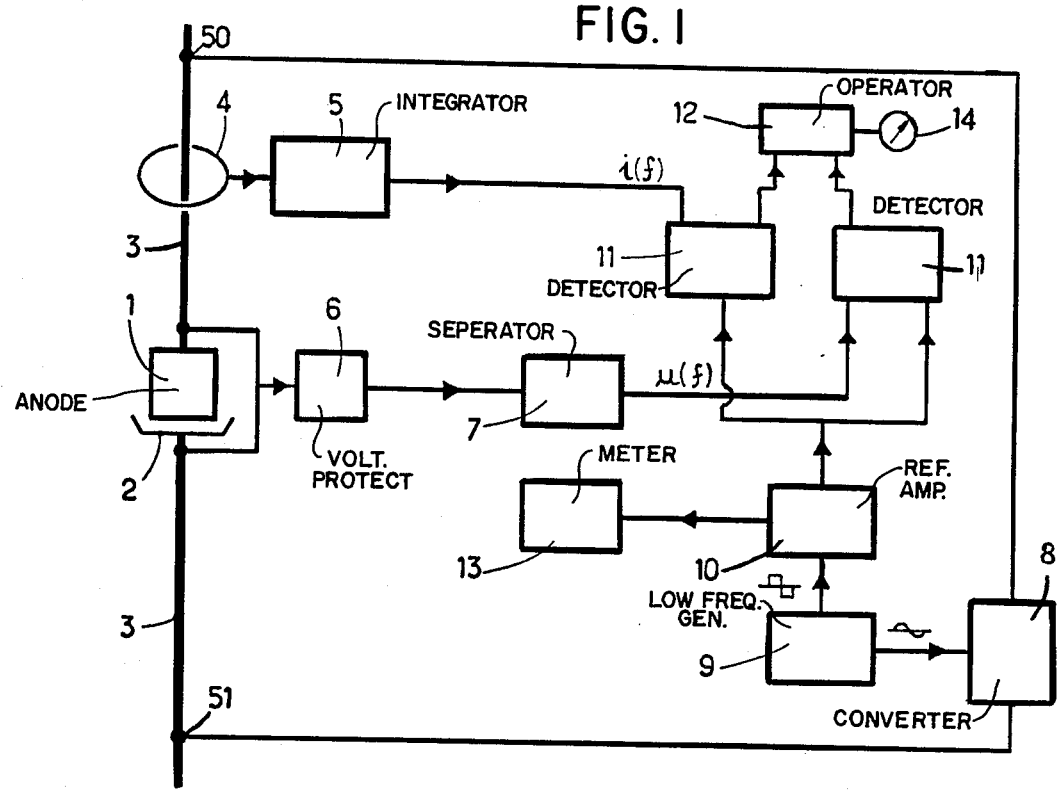
FIG. 1 is a block circuit diagram of a first exemplary embodiment of the apparatus according to the invention.

FIG. 1 is a block circuit diagram of the apparatus used, the complete circuit plan of each of the elements used being given in the following Figures for the purposes of detailed analysis. This apparatus is mounted on an electrolysis cell comprising an anode 1 and a cathode 2 and fed by conductive bars 3. It consists of a circuit for measuring converted current if, comprising an inductive probe 4 for measuring current and an impedance adapter/integrator 5, a circuit for measuring the electrolysis voltage V, comprising an overvoltage protector 6 and an impedance adapter/a.c. separator 7, a current converter 8 connected between the poles of the cell and controlled by a low-frequency generator 9, a galvanically insulated reference amplifier 10 and two relative synchronous detectors 11, one at the voltage uf, and the other at the current if, attacking a dividing operator uf/if which is denoted by the reference 12. It may be completed by a frequency meter 13 giving the value of f and a reader 14 giving rf.

The electronic apparatus as a whole is fed by a symmetrical voltage source ST with a positive pole STP, a negative pole STN and a centre point STO connected to ground. In the embodiment in question, the voltage of this source is twice 15 volts.

The various elements of which the apparatus is made up will now be described. Some of these elements are specially designed and are described in detail, whilst others are commercially available elements and are described more generally. It should be noted that certain elements appear several times in the complete circuit arrangement.

The circuit for measuring converted current will first of all be described.

Figure 2:
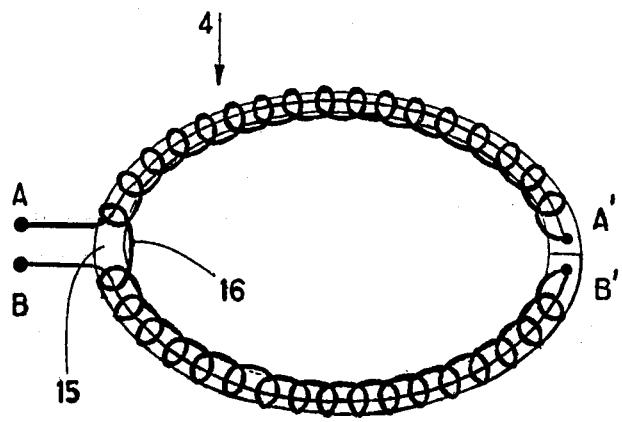
FIG. 2 shows an inductive probe for measuring the alternating-current component of the current flowing through the cell.

As shown in FIG. 2, the inductive probe 4 consists of an annular solenoid encircling the conductive bar 3 through which the current if to be measured flows. This solenoid is made from a flexible coil former 15 of an amagnetic material, onto which is wound a conductive wire A'B' 16 forming N uniformly distributed surface windings S. The lengths AA' and BB' forming the return wire of the probe pass through the centre of the windings.

If the current if flowing through the bar 3 is of the following form:

$$if = I\ i.\ (f).\sin 2\pi ft$$

where $t$ is the time, the voltage ef appearing between the terminals A and B is equal to:

$$ef = K\ i\ .\ (f),\ 2\pi f \sin(2\pi ft - \frac{\pi}{2})$$

$$\text{where } K = M\ .\ S\ \frac{N}{l}$$

$\mu^\circ$ is the magnetic permeability of the gap (4 π 10⁻⁷), N/l is the number of windings per meter, S is the surface area of one winding in square meters. It can be seen that the voltage ef is displaced by π/2 behind the intensity In the embodiment in question, the probe consists of two annular solenoids 17 and 18 placed end to end, their respective lengths being 1.50 and 2.50 meters and their respective electrical resistances being 29.9 and 46.5 ohms respectively. The coefficient K of the probe is equal to 2.065.10⁻⁶ in MKSA units. It weighs 10 kg. This probe is suitable for measurement in the largest cells used for the production of aluminium, for example cells in which the intensity of the electrical current reaches 200 kiloamps.

Figure 3:
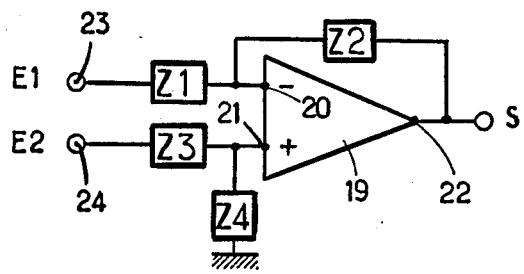
FIG. 3 is a basic circuit diagram of a looped operational amplifier stage.

The impedance adapter/integrator 5 comprises differential loop operational stages, of which the basic circuit diagram is shown in FIG. 3. One stage 19, for example a transistor amplifier or an integrated circuit, has two differential inputs 20 and 21 and an output terminal 22. It comprises further terminals enabling correction circuits and feed terminals to be connected to the source ST. These terminals are not shown in the Figures. The inputs 20 and 21 are connected to the two general input terminals 23 and 24 by impedances Z1 and Z3. On the other hand, the negative input 20 is connected to the output 22 by an impedance Z2, whilst the positive input 21 is connected to earth by an impedance Z4.

The gain of this stage is expressed as follows:

$$S = E1W1 + E2W2\ \frac{1 + W1}{1 + W2}$$

where the transfer functions W1 and W2 are equal to:

$$W1 = \frac{Z2}{Z1} \qquad \text{and} \qquad W2 = \frac{Z4}{Z3}$$

Figure 4:
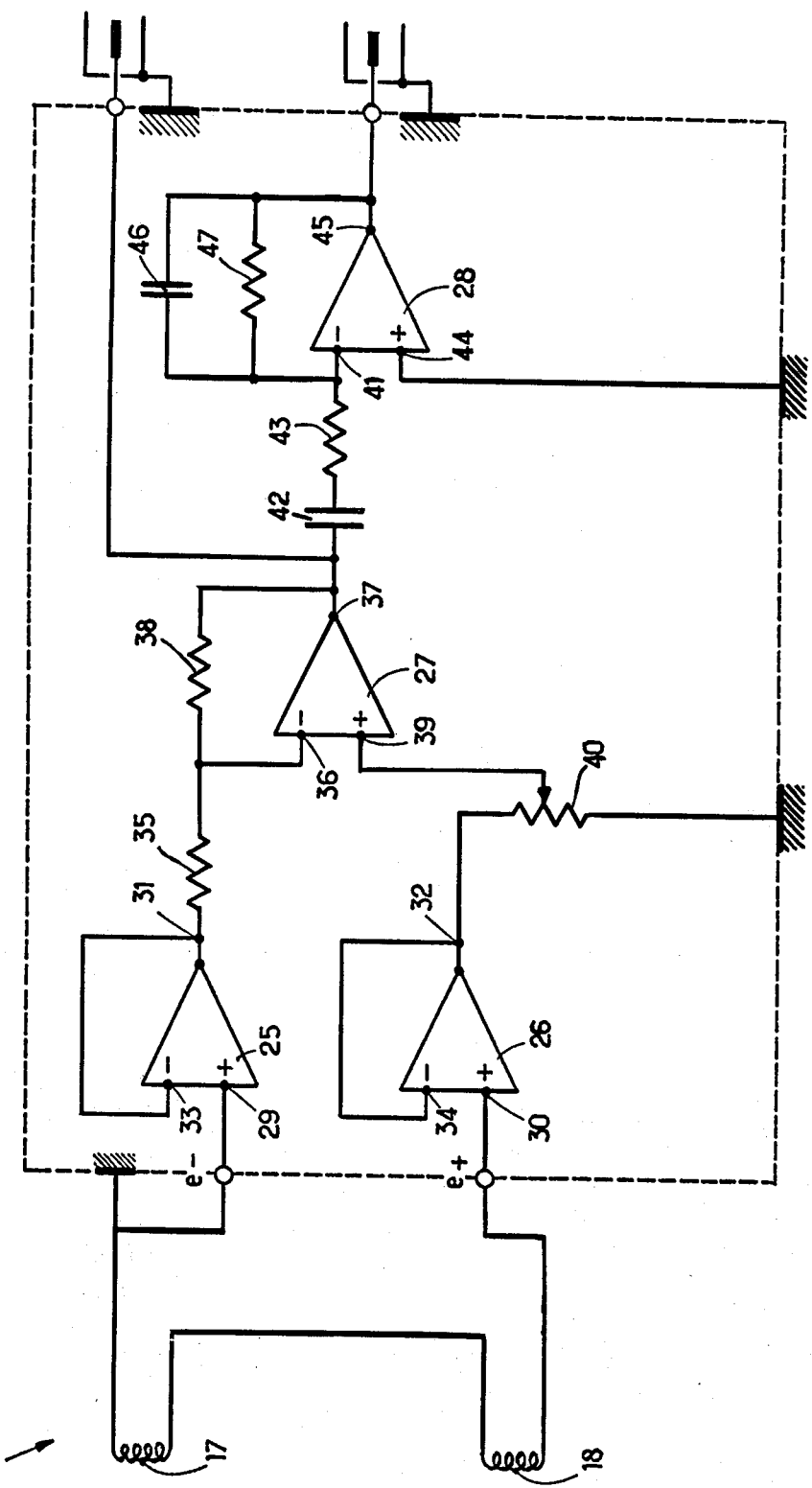
FIG. 4 is a circuit diagram of an impedance-adapting and integrating amplifier.

As shown in FIG. 4, the impedance adapter/integrator 5 comprises a differential amplifier of high input impedance, consisting of the three stages 25, 26 and 27, and an integrator formed by the stage 28.

The positive input 29 of the stage 25 is connected to one of the ends of the coil 17 and to earth, whilst the positive input 30 of the stage 26 is connected to the corresponding end of the coil 18. The other end of each of these coils 17 and 18 is connected in series. The outputs 31 and 32 of the stages 25 and 26, respectively, are connected to the negative inputs 33 and 34 of the same stage. The output 31 of the stage 25 is connected by a resistance 35 to the negative input 36 of the stage 27, this input 36 being connected on the other hand to the output 37 by a resistance 38 equal in value to the resistance 35. The positive input 39 of the stage 27 is connected to the slide of a potentiometer 40 connected between the output 32 of the stage 26 and earth.

By applying what has been explained above with reference to FIG. 3, it can be seen that, at the output of the stages 25 and 26, voltages equal to and in phase with the input voltages applied at 29 and 30 are obtained at 31 and 32, respectively. Using the notations in FIG. 3: $Z1 = \infty$, $Z2 = O$, $Z3 = O$, $Z4 = \infty$, hence: $W1 = O$ and $W2 = \infty$. The input impedance is very high, amounting to several hundred megaohms, whilst the output impedance is very low, amounting to a few ohms, because the stages 25 and 26 have a high gain. The voltage applied to the stage 27 is equal to the difference between the input voltages 29 and 30, the potentiometer 40 allowing zero adjustment by making the voltage at 36 and 39 equal.

The negative input 41 of the stage 28 is connected to the output 37 of the stage 27 by a capacitor 42 in series with a resistance 43, the positive input 44 being connected to earth. The output 45 of this stage 28 is connected to the negative input 41 by an integrator circuit comprising a capacitor 46 and a resistance 47 connected in parallel.

By applying what has been explained with reference to FIG. 3 to the stage 28, it can be seen that the output voltage at 45 is equal to the input voltage with changed sign multiplied by W1. Now:

$$W1 = \frac{Tp}{(1 + T1p)(1 + T2p)}, \text{ with:}$$

Figure 5:
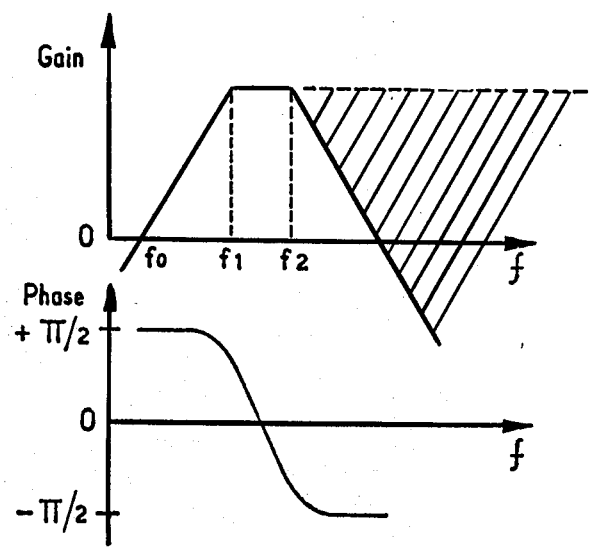
FIG. 5 is a graph showing the gain and phase trends of the integrating stage of the amplifier shown in FIG. 4.

$T = R(47).C(42)$ $T1 = R(43).C(42)$ $T2 = R(47).C(46)$ where R43 is the value of the resistance 43 in ohms, C42 is the value of the capacitor 42 in farads, etc. For example, if $R43 = 4.75 \text{ K}\Omega$, $R47 = 10$ megaohms, $C42 = 100 \mu f$ and $C46 = 0.47 \mu f$, then $f = \frac{1}{2\pi T} = 1.59.10^{-4} \text{c/s}$ $f_1 = \frac{1}{2\pi T2} = 0.033 \text{ c/s}$ $F_2 = \frac{1}{2\pi T1} = 0.335 \text{ c/s}$ A band-pass filter as shown in FIG. 5 is obtained. The integration zone is situated beyond the frequency $f_2$, so that the phase is: $\pi/2$. In view of the change of sign in stage 28, the output signal is in phase with if in the integration zone.

Taking into account the coefficient K of the probe, the choice of the limiting frequency f. enables the gain to be placed at an adequate value giving, at 45, a signal of the order of 1 millivolt per amp measured of I.

The precision of the circuit for measuring converted current is completely dependent upon the probe. The probe requires a constant cross-section of the windings, uniform distribution thereof along the annulus and the plane of each winding perpendicular to the axis of the coil support.

The circuit for measuring the electrolysis voltage will now be described.

The overvoltage protector 6 comprises a voltage limiter 48 and an amplifier 49.

Figure 6:
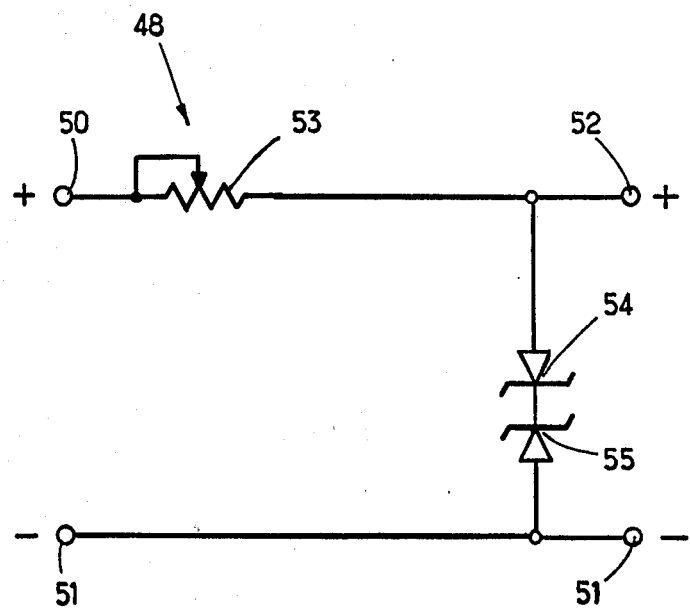
FIG. 6 is a circuit diagram of a voltage limiter.

The voltage limiter 48 is connected FIG. 6 between the positive pole 50, i.e., the anode, and the negative pole 51, i.e., the cathode, of the cell. It comprises a variable resistance 53 connected between the positive pole 50 and the positive output 52 of the limiter. Between the positive output 52 and the negative output 51 are connected a Zener diode 54 acting as a limiter, i.e., with its "plus" pole connected to the positive output 52, and in series with this diode an identical diode 55 connected in the opposite direction, i.e., with its "minus" pole connected to the "minus" pole of 54 and with its "plus" pole connected to the negative output 51 of the limiter.

This limiter performs two functions. On the one hand, it limits the signal to a safe value for the measuring circuit in the event of polarisation of the anode of the cell. On the other hand, it corrects the phase of the voltage signal so as to compensate for the phase displacement of the current circuit. In normal operation, i.e., when the input signal is below the operating voltage of the Zener diode, the circuit may be compared with a circuit of the type comprising a series resistance, in this case the resistance 53, and a parallel capacitance C, in this case the capacitances of the diodes, of the line and of the input of the amplifier 49. The transfer function of this circuit is:

$$W = \frac{1}{1 + Tp}$$

where $T = R\ 53.C$.

By varying the valule of R 53, it is possible to modify the limiting frequency $$f = \frac{1}{2\pi R\ (53).C}$$

and hence the phase of the output signal relative to that of the input signal U. It is thus possible to apply to the voltage signal a phase correction which compensates the phase displacement of the current circuit essentially attributable to the inductive probe.

The measuring amplifier 49 comprises (FIG. 7) a differential amplifier with a high input impedance and two a.c./d.c. separators.

The differential amplifier comprises the stages 56, 57 and 58. It is identical with the differential amplifier described in reference to FIG. 4. Its description may be derived by replacing the references 25, 26, 27, 29, 30, 31, 32, 33, 34, 35, 36, 37, 38, 39 and 40, used in the description of FIG. 4, by the references 56, 57, 58, 51, 52, 59, 60, 61, 62, 63, 64, 65, 66, 67 and 68, respectively.

The only difference is the presence of the transistor 69 whose base 70 is connected to the output 65 of the stage 58, the collector 71 being connected to the negative pole STN of the d.c. voltage source ST, whilst its emitter 72 is connected to the resistance 66 which, unlike the corresponding resistance 38 in FIG. 4, is not connected to the output 65 of the stage 58, but instead to the emitter of the transistor 69.

The a.c. separator 7 comprises the stages 73, 74 and 75.

Through a potentiometer 76, the emitter 72 of the transistor 69 attacks the positive input 77 of the stage 73 whose output 78 is connected to the base 79 of a transistor 80. The collector 81 of this transistor is connected to the negative pole STN of the d.c. voltage source ST, whilst its emitter 82 is connected, on the one hand by a resistance 83, to the positive pole STP of the d.c. voltage source ST and, on the other hand through a resistance 84, to the negative input 85 of the stage 73. This input is connected by a resistance 85, equal in value to the resistance 84, to the output 87 of the stage 74 connected on the other hand to the negative input 88 of the stage by a resistance 89. The positive input 90 of this stage is connected to earth. The positive input 91 of the stage 75 is connected to earth, whilst its negative input 92 is connected, on the one hand, to the emitter 82 of the transistor 81 by a resistance 93 and, on the other hand, to the output 94 of the stage by a capacitor 95. The output 94 of the stage 75 is connected to the negative input 88 of the stage 74 by a resistance 96. The a.c. output 97 is situated on the emitter 82 of the transistor 80.

Figure 8:
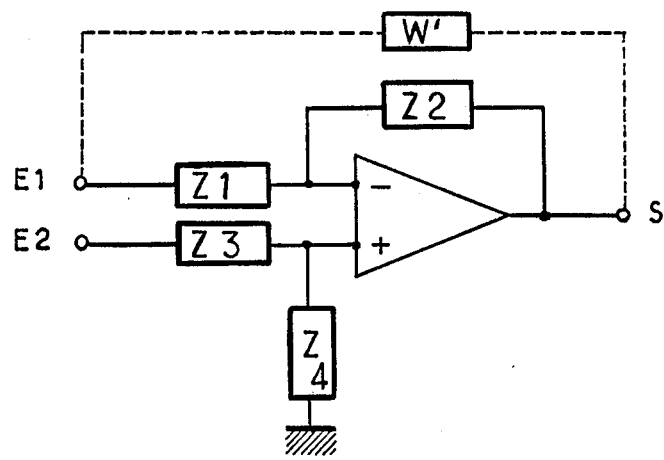
FIG. 8 is a basic circuit diagram of one stage of the amplifier shown in FIG. 7.

Disregarding the transistor 80, which constitutes a power amplifier with a voltage gain of +1, the stage 73 may be illustrated as in FIG. 8 which is similar to FIG. 3. By applying the formulae recalled in connection with FIG. 3, the following result is obtained:

$$S = -E1 + E2 \text{ with: } W1 = \frac{Z2}{Z1} = 1 \text{ and } W2 = \frac{Z4}{Z3} = 1$$

If the output is looped back to the input E1 by the transfer function W' represented by the stages 75 and 74, the following result is obtained: $S = -SW' + E2$, in other words $$\frac{S}{E2} = \frac{1}{1 + W'}$$

Now: $W' = W(75) \cdot W(74)$, with $$W(75) = -\frac{1}{Tp} \text{ and } W(74) = -\frac{R(89)}{R(96)}$$

If $\frac{R(89)}{R(96)} = 100$, then $$W' = 100 \ \frac{1}{Tp} = \frac{1}{\frac{Tp}{100}} = \frac{1}{T'p}$$

with:
$$T' = \frac{R(93) \cdot C(95)}{100} = 0.22 \text{ second}$$

if
R 93 = 220 k Ω and C 95 = 100 μf

It follows that:

$$\frac{S}{E2} = \frac{1}{1 + \frac{1}{T'p}} = \frac{T'p}{1 + T'p}$$

hence $$f = \frac{1}{2\pi \cdot 0.22} = 0.723 \text{ c/s}$$

Figure 9:
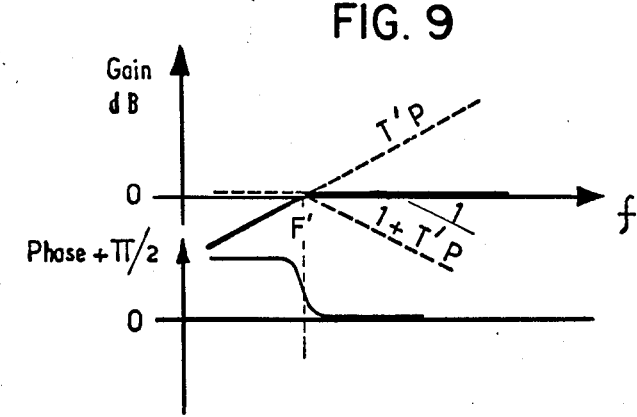
FIG. 9 is a graph showing the gain and phase trends of this stage.

A high-pass filter with a gain of 1, i.e. . . . decibels, is thus obtained as shown in FIG. 9. Above the limiting frequency $f'$, the output is in phase with the input. The potentiometer 76 allows zero adjustment in the absence of periodic signals at the input of the amplifier.

The a.c. separator comprises an amplification stage 98 whose positive input 99 is connected to the slide of a potentiometer 100 whose ends are connected respectively to the positive pole STP and negative pole STN of the direct-current source. The negative input of this stage is connected through a resistance 101 to the common point 102 between a resistance 103, connected on the other hand to the emitter 72 of the transistor 69, and a capacitor 104 connected on the other hand to earth. The output 105 of the stage 98 is connected to the base 106 of a transistor 107 whose collector 108 is connected to the negative pole STN of the direct current source ST, whilst its emitter 109 is connected to the following points: directly to the d.c. output 110, to the positive pole STP of the direct-current source ST through a resistance 111, to the negative input 113 of the stage through a capacitor 112 and, finally, to the point 102 through a resistance 114. It should be noted that the resistances 101, 103 and 114 are equal in value.

If the emitter 72 of the transistor 69 is taken as the basis of this circuit arrangement, the transfer function may be written as follows:

$$W(p) = \frac{1}{(RCp)2 + b(RCp) + 1}$$

where R is the common value of the resistances 101, 103 and 115, and where the following values is assumed for b:

$$b = 3 \sqrt{\frac{C(112)}{C(104)}}, \quad C = \frac{C(104) \cdot b}{3} = \frac{3C(112)}{b}$$

A low-pass filter of the second order is obtained.

If : R = R 101 = R 103 = R 114 = 100 K C 104 = 4.7 μf and C 112 = 1 μf, then: b = 1.38, C = 2.17 μf, T = 0.217 seconds and f = 0.733 c/s.

A low-pass filter is thus obtained with substantially the same limiting frequency as the high-pass filter studied in connection with the ac. separator. The output is in phase opposition with the input.

It is pointed out that, at the output of each of the stages 58, 73 and 98, there are transistors 69, 80 and 107 of the pnp type with a common collector. This circuit arrangement enables the output power of the corresponding stage to be increased, has a high input impedance, a low output impedance, a voltage gain of slightly less than 1 and a very wide band width. These transistors may be omitted if the stages which they complete are sufficiently powerful and have sufficiently low output impedances.

The converter 8 for the electrolysis current may be one of the three following types:
direct conversion of the source at the level of the rectifier,
injection of a current,
derivation of a current.

The control systems of an industrial electrolysis plant, using autotransformers and variable reactances, are not suitable for direct conversion and, in any case, limits it to the field of frequencies below the mains frequency.

The arrangement described hereinafter may be used both with current derivation and with current injection in electrolysis cells using an auxiliary source.

Figure 10:
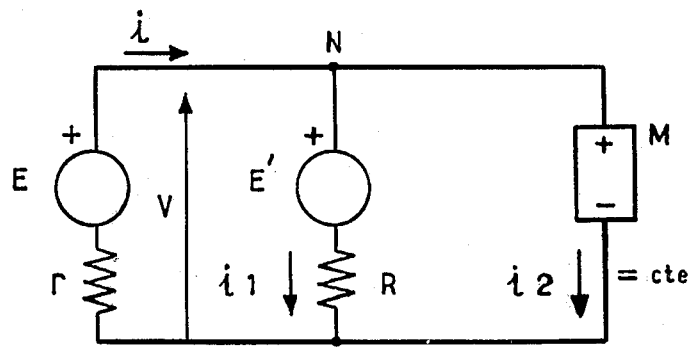
FIGS. 10 and 11 are block circuit diagrams of electrolysis current converters respectively arranged for deriving and injecting current.

FIG. 10, which illustrates the derivation circuit, shows an electromotive force generator E of resistance r feeding a load circuit with a counterelectromotive force E' and a resistance R. The converter M derives a current of intensity i2, whilst the load circuit receives a current i1 and the generator supplies a current i. Thus $$i1 = \frac{E - E' - ri2}{r + R}$$

Figure 11:
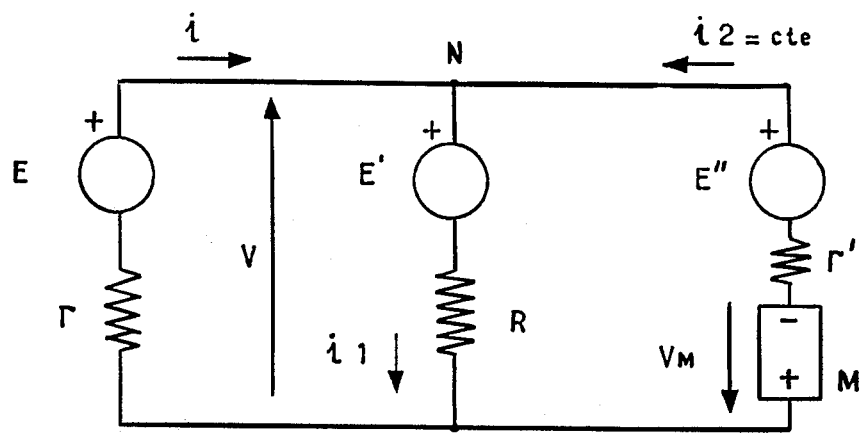

FIG. 11, which illustrates the injection circuit, shows the same generator and the same load circuit and, in parallel with these circuits, an auxiliary generator of electromotive force E'' and resistance r' in series with a converter M. Thus:

$$i1 = \frac{E - E' + ri2}{r + R}$$

These two circuits prompts the following remarks:
When R = r, in other words when the source is adapted to the load, $$\frac{r}{r + R} = \frac{1}{2}$$

and, in the general case, the converted current flowing through the electrolysis cell is equal to half the current coming from the converter.

The power dissipated in the converter is equal to $$P = (VM + \Delta v) i2$$

where VM is the minimum voltage required for satisfactory operation of the converter: minimum emitter-collector voltage of the regulating transistor plus internal voltage drop; $\Delta v$ is the difference between the extreme values of the voltage of an electrolysis cell in normal operation.

In cases where the voltage v at the terminals of the generator (or receive) is less than VM, the injection circuit is essential, hence the need to provide an auxiliary source of electromotive force E'' and internal resistance r', so that: E'' — (VM + r'i2) > v.

In every other case, it is of advantage to use the derivation circuit which saves the auxiliary source.

The converter (FIG. 12) comprises a power transistor 115 acting as a series regulator. Its collector 116 is connected to the positive pole 50 of the electrolysis cell, whilst its emitter 117 is connected through a protection resistance 118 to the following elements: an intensity-measuring output 119, the negative input 120 of an amplifier stage 121 and a low-value resistance 122 forming a shunt and connected on the other hand to the negative pole 51 of the cell. The base 123 of the transistor 115 is attacked by the emitter 124 of a transistor 125 of which the base 126 is in turn attacked by the emitter 127 of a second transistor 128. The collectors of these two transistors are connected to the collector 116 of the transistor 115. The base 129 of the transistor 128 is connected to the output 130 of the stage 121.

A reference voltage, processed by two stages 131 and 132, is applied to the positive input 133 of the stage 121. The positive input 134 of the stage 131 is connected to earth through a resistance 135. Its negative input 136 is connected to the output 137 of the stage by a resistance 138, to a tap 139 connected to an alternating current source through a resistance 140 and, finally, through a resistance 141 to the slide of a potentiometer 142 connected between the negative pole STN of the d.c. voltage source ST and earth which is itself connected to the pole STO. The resistances 138, 140 and 141 are of equal value. The positive input 143 of the stage 132 is directly connected to earth, whilst its negative input 144 is connected, on the one hand, to the output 137 of the stage 131 through a resistance 145, and on the other hand to its own output 146 by a resistance 147. In addition, this output 146 is connected to the positive input 133 of the stage 121.

Referring to FIG. 3, it is possible to write for the stage 131:

$$S(131) = (a_1 E1 + a_2 E2)$$

where E1 is the voltage at the slide of the potentiometer 142 and E2 the a.c. voltage at 139. Thus:

$$a_1 = a_2 = \frac{Z2}{Z1} = 1$$

hence S 131 = —(E1 + E2)
Likewise for the stage 132:

$$S(132) = -S(131) \frac{Z2}{Z1}$$

If R (145) = 10. R (147), $$\frac{Z2}{Z1} = 0.1,$$

it follows that (S(132) = 0.1(E1 + E2).

By virtue of the potentiometer, it is possible to select the value of E1 and hence the value of the polarisation current, whilst E2 is supplied by a low-frequency generator: E2 = E·sin 2 $\pi$ ft.

The transistor 115 is designed to operate as a series regulator. In actual fact, several groups of transistors 115 and resistances 118, connected in parallel, are used in view of the size of the current flowing through them. The amplifier stage 121 permanently measures the error between the reference voltage applied to the positive input 133 and the voltage equal to the product of the value of the resistance 122 by the intensity of the curent i which flows through it and which represents the image of the current to be regulated. If i increases, the output voltage 130 decreases, reducing the base polarisation of the trnsistor 115 so as to reduce the current i flowing through it. The opposite effect is obtained when i decreases. Since the reference voltage has an a.c. component, the intensity i of the current varies according to the frequency of that component. The regulation level is better than 0.1%.

A synchronous detector circuit 11 will now be described. In this connection, the principle of synchronous detection will first of all be recalled in reference to FIG. 13 . . . .

In other words a studied system 148 modulated by a generator 9 which also controls the synchronous detector. The studied system 148 emits a sinusoidal signal E2 = E·sin (2 π f + φ) where f is the frequency of the generator 9, φ is the phase displacement of Ef relative to the signal of the generator 9.

This signal Ef is concealed in the noise: it characterises the system to be studied. It first passes through a selective amplifier 149 tuned to the frequency f, after which it is applied to one of the inputs of the actual synchronous detector 150. The generator 9 also emits a square signal of frequency f in phase with the sinusoidal modulation signal. This square signal is applied to a phase shifter 151 and, after phase shifting, is applied to the second input of the synchronous detector 150. The output signal of the synchronous detector enters an integrator 152 and from there enters a load 153 illustrated in the form of a measuring apparatus.

Figure 14:
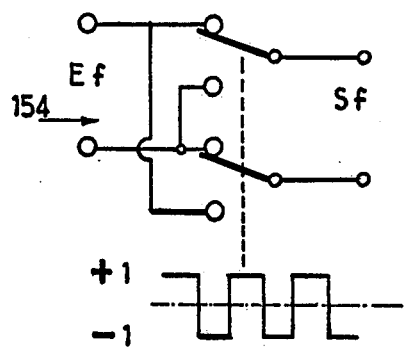
FIG. 14 is a circuit diagram of a bipolar circuit breaker equivalent to the detector.

The actual synchronous detector 150, may be compared (FIG. 14) with a double inverter 154 which would be controlled by the generator 9 and which would invert the direction of the voltage Ef at the frequency f. This is equivalent to multiplying the signal Ef successively by +1 and by −1 at a frequency equal to its own frequency, i.e., to rectifying the signal Ef.

Figure 15:
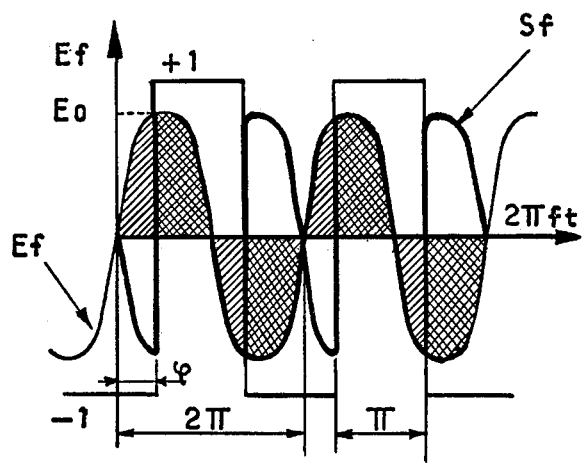
FIGS. 15 to 19 show in various hypotheses how the current to be detected is cut off by the detector.

Accordingly, the output signal Sf comprises, as shown in FIG. 15, dark-coloured "arches" which are counted positively and clear "arches" which are counted negatively. Its mean value is equal to:

$$Sf \text{ moy} = \frac{1}{\pi} \oint_{\phi}^{\phi} \pi E \cdot \sin 2\pi ft \, dt$$

$$= \frac{2}{\pi} E \cdot \cos\phi$$

If the measured signal Ef is not synchronous with the signal from the generator 9, the term cos φ fluctuates between +1 and −1 and its mean value inclines towards zero when the time increases, hence the advantage of providing an integrator 152 with a high time constant at the output of the detector 150. If the signal is synchronous with the signal from the generator, φ is constant and has a clearly defined mean value. The first case is that of noise, whilst the second case is that of the signal studied Ef.

Figure 16:
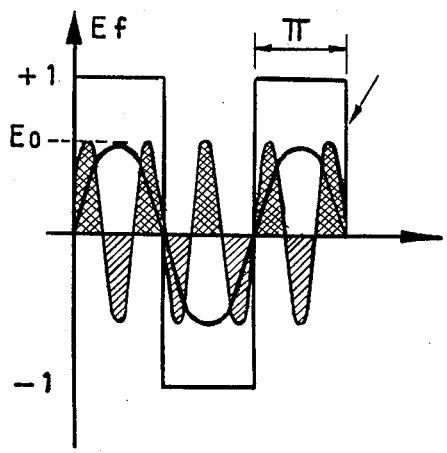
Figure 17:
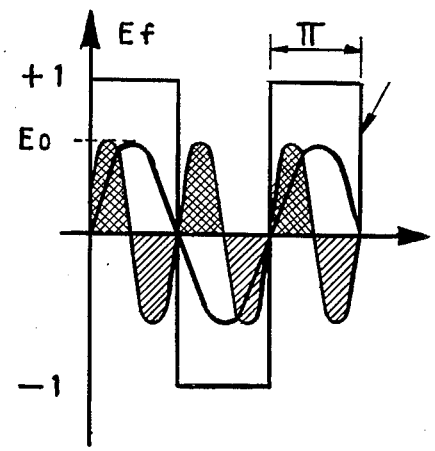

The harmonics of the signal have a different effect according to whether they are odd or even harmonics. FIG. 16 relates to a third harmonic, i.e., to an odd harmonic, whilst FIG. 17 relates to a second harmonic, i.e., to an even harmonic. The arches of the signal counted positively in the mean value are darkly hatched, whilst those counted negatively are lightly hatched. A mean value is obtained for each position of the reference signal:

$$-\frac{1}{3} \cdot \frac{2}{\pi} E.$$

in the case of FIG. 16 (odd harmonic) zero in the case of FIG. 17 (even harmonic).

The even harmonic produce a fluttering around a mean value of zero, whilst the odd harmonics produce a mean value which is not zero.

The band width is governed by the time constant: T = RC of the integrator 152 in the form of a series resistance of R ohms followed by a parallel capacitor of C farads: the more RC increases, the narrower the band width. If $$f. = \frac{1}{2\pi RC},$$

the following frequency bands are thus treated: f± f., 3f±f., 5 f±f. . . .

It is to eliminate this deficiency that a selective amplifier 149 tuned to the frequency f is provided ahead of the detector 150. The amplifier rejects the frequencies 3f, 5f, etc., so tht the frequency band of the signal is reduced to f±f.

Figure 18:
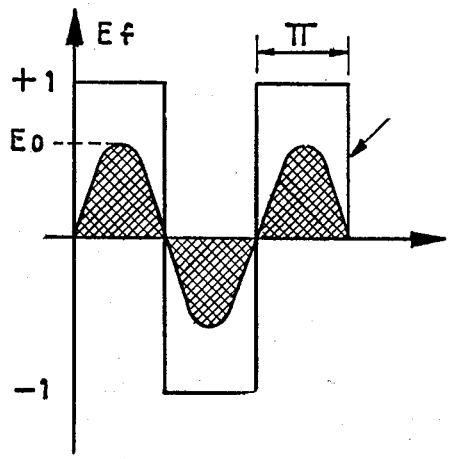
Figure 19:
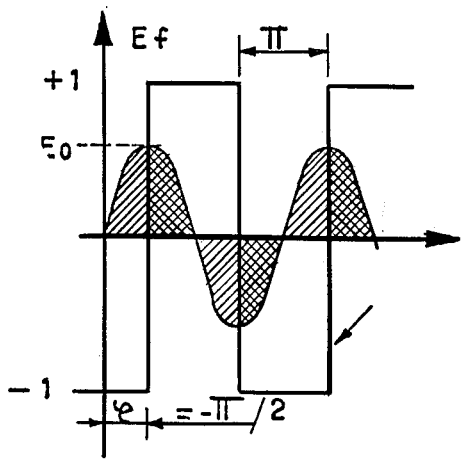

The function of the phase shifter 151 is to stagger the reference by an angle φ relative to the signal Ef to be detected. It can be seen that FIG. 18, where detection takes place in phase, i.e., where φ= O, the mean value of the signal is maximal, whilst in FIG. 19, where detection takes place in quadrature $$(\phi = \frac{\pi}{2}) \quad ,$$

the mean value of the signal is zero.

By virtue of its sensitivity, detection with a zero signal is used for in-phase adjustment of the reference signal to the signal Ef to be measured.

The synchronous detector is a commercially available apparatus, so that there is no point in describing it in any more detail. It comprises the elements 149 to 153 surrounded by a rectangle of chain lines in FIG. 13.

The apparatus uses two detectors of which one is associated with uf and the other with if.

Figure 20:
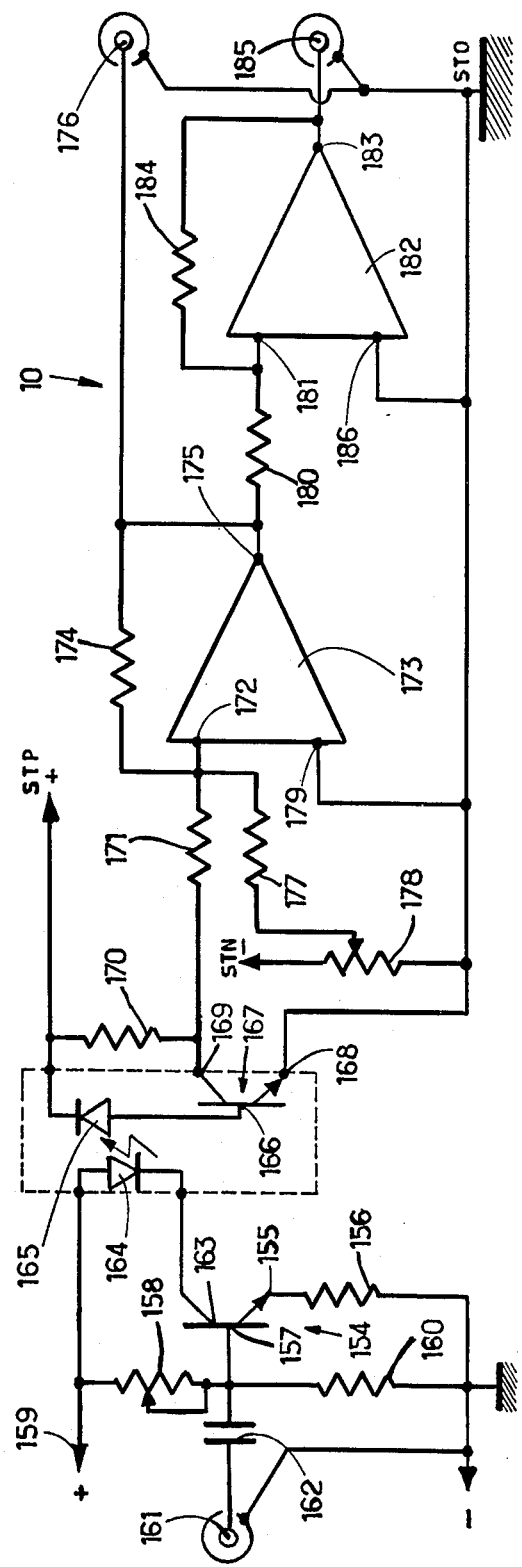
FIG. 20 is a circuit diagram of a galvanically insulated reference amplifier.

FIG. 20 is a circuit diagram of the galvanically insulated reference amplifier 10.

The reference signal emanating from the low-frequency generator 9 is at the potential of the electrolysis cell by way of the current converter 8, hence the need to decouple it from the voltage signal of the cell. This is the function performed by the galvanic insulation.

The reference amplifier 10 begins with an impedance-adapter stage with an a.c. input comprising a transistor 154 whose emitter 155 is connected to earth through a resistance 156, whilst its base 157 is attacked by a potentiometer in the form of a variable resistance 158 connected to the positive pole 159 of an auxiliary voltage source whose negative pole is connected to earth, and a resistance 160 on the other hand connected to earth. The a.c. voltage, admitted by a tap 161, is relayed to the base 157 through a capacitor 162.

The collector 163 of the same transistor 154 is connected to the negative pole of an electroluminescence diode 164 connected on the other hand to the positive pole 159 of the auxiliary voltage source. Opposite this diode 164 there is a photodiode 165 receiving the light emitted by the first. In this way, a signal identical with the output signal of the transistor 154 is obtained at the terminals of the diode 165 although there is no material connection between the two diodes. Accordingly, the galvanic insulation is complete. The positive pole of this photodiode 165 attacks the base 166 of an impedance-adapting transistor 167 whose emitter 168 is connected to earth, whilst its collector 169 is connected to the positive pole of the common d.c. voltage source ST through a resistance 170. The negative pole of the photodiode 165 is connnected to the positive pole STP of the source ST.

The collector 169 of the transistor 167 is also connected by a resistance 171 to an input 172 of a stage 173. This input 172 is further connected, on the one hand by a resistance 174, to the output 175 of the stage and to a "reference" output 176, and on the other hand by a resistance 177 to the slide of a potentiometer 178 connected between the negative pole STN of the source ST and earth STO. The other input 179 of the stage is connected to earth. The output 175 is connected by a resistance 180 to an input 181 of a stage 182, this input also being connected to the output 183 of the stage by a resistance 184 equal in value to the resistance 180. This output is connected to a "frequency" tap 185. The second input 186 of the stage is connected to earth.

Accordingly, this galvanically insulated reference amplifier comprises:

an impedance-adapting stage 154 with an a.c. input 161, an opto-electronic stage 164–165 ensuring galvanic insulation, an adaptor-amplifier stage 173–182 through which it is possible, by acting on the potentiometer 178, to eliminate the d.c. component of the output signal and to bring it back into phase with the input signal.

The low-frequency generator 9 is of a commercially available type. It gives both a sinusoidal signal and a square signal of the same variable frequency f. These two signals are in phase. It is pointed out that the reference amplifier 10 may be connected to the sinusoidal output of the low-frequency generator when, as is often the case, the synchronous detector comprises a circuit which transforms the sinusoidal signal into a square signal.

The dividing operator 12 comprises a divider module 186. The input 187 marked "x", is connected to the output 188, marked "S," and to an output tap 189. The input 190, marked "y," is connected to a tap 191 corresponding to an intensity io, whilst the input 192, marked "z," is connected to a tap 193 corresponding to a voltage uo. The input 194, marked "g," in connected to the slide of a potentiometer 195 connected between the negative pole STN of the direct-current source ST and earth, whilst the tap 196 marked "B" is connected to the slide of a potentiometer 197 connected between the positive pole STP of the direct-current source ST and earth. The other taps of the module are connected respectively to the three poles STP, STO and STN of the d.c. voltage source ST. It should be noted that it is the connection "x - s" which gives the module 186 its divider character.

The output signal appearing at the tap 189 is equal to $$-10 \frac{uo}{io}.$$

It is the image of $$rf = \frac{uo}{io}$$

as explained above.

The operation of the apparatus will now be described with reference to the simplified circuit diagram shown in FIG. 1.

The low-frequency generator 9 has its output for sinusoidal current of frequency f connected to the input tap 139 of the current converter 8 and its output for square signals of frequency f connected to the tap 158 of the galvanically insulated reference amplifier 10. The current converter 8 connected to the terminals 50 - 51 of the cell 1-2 thus converts the current I flowing through the cell according to a sine curve of frequency f.

A current if proportional to the current I is measured by the inductive probe 4 and its impedance adaptor/integrator 5. The impedance adaptor/integrator 5 brings the signal emitted from the probe 4 back into phase and regularises it.

The potentiometer 40 allows zero adjustment in the absence of signals at its input.

The integrated output 45 is applied to the input of the selective amplifier 149 of the relative synchronous detector 11 at the intensity if. The phase shifter 151 of the synchronous detector is attacked by the square signal of frequency f coming from the low-frequency generator 9 through the galvanically insulated reference amplifier 10 whose function is to separate the generator 9, which is at the voltage of the cell, from the synchronous detection amplifier 11. Since the voltage applied to the input of the synchronous detector is proportional to if = io sin (2π + φ') and since the phase shifter 151 is adjusted to compensate for the phase displacement (φ), an output signal proportional to 2 io is obtained, as explained above in reference to the synchronous detector.

The voltage V at the terminals of the cell is applied to the input of the voltage limiter 48 which chops the voltage collected in the event of over voltage due in particular to the polarisation of the anode. The output 52 of the limiter is connected to the input of the impedance adaptor/a.c.-d.c. separator 7 which comprises a differential amplifier 56-57-58 whose zero is adjusted by acting on the potentiometer 68, and the a.c.-d.c. separator 73-74-75 whose zero is adjusted by acting on the potentiometer 76 in the absence of signals at its input. The output 97 of the adaptor/separator is connected to the input of the selective amplifier 149 of the amplifier/synchronous detector 11 whose phase shifter 151 is attacked by the square signal coming from the low-frequency generator 9 through the galvanically insulated reference amplifier 10. Since the voltage applied to the input of the synchronous detector is proportional to uf = uo sin (2πf + φ') and since the phase shifter 151 is adjusted to compensate for the phase displacement (φ'), an output signal proportional to $$\frac{2}{\pi} Uo$$

is obtained, as explained above.

The signal corresponding to io is applied to the input 191 of the dividing operator 12, whilst the signal corresponding to uo is applied to the input 193 of the same divider. A signal proportional to $$rf = \frac{uo}{io}$$

is obtained at the output 189. This signal is measured by the reader 14 which may be directly graduated in the value of rf.

At decreasing values of the frequency f, the curve giving rf as a function of f is traced, followed by extrapolation to the zero value of f. r (f=O) = R, the resistance of the cell, is thus obtained.

This arrangement may be improved to enable the resistance R and the counterelectromotive force E of the cell to be calculated. In this case, it is completed by an analogue or numeric system.

Figure 22:
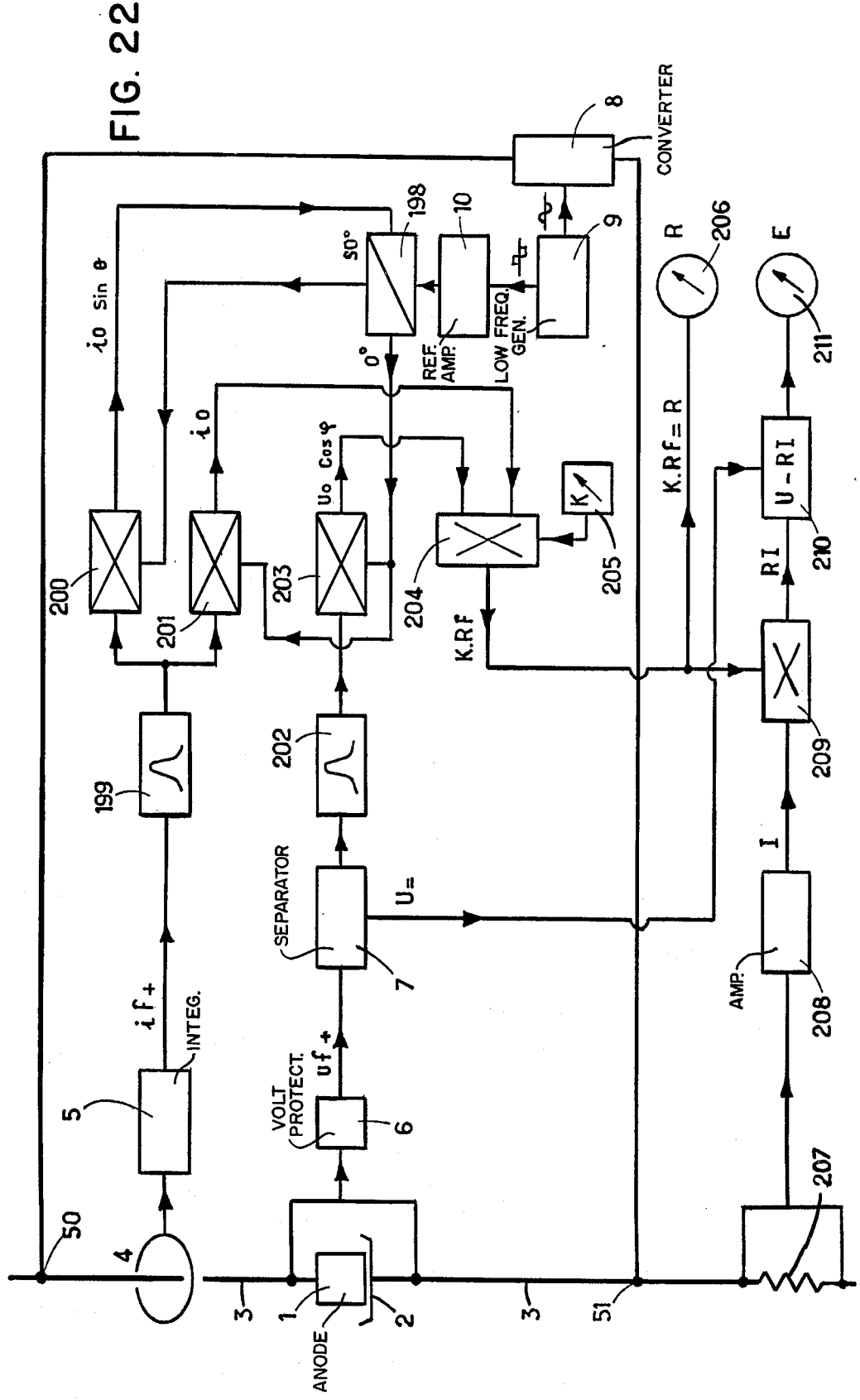
FIG. 22 is a block circuit diagram of a second exemplary embodiment of the apparatus according to the invention developed to a greater extent than the embodiment illustrated in FIG. 1.

According to FIG. 22, the reference signal is subordinate to the current phase if.

The low-frequency generator 9 has its sinusoidal output connected to the input of the current converter 8 which is itself connected between the positive and negative poles 50-51 of the cell 1-2. The square output signal of the generator 9 is connected to the input of the galvanically insulated reference amplifier 10 whose output is connected to the input of a slave phase shifter 198 delivering two square signals phase-displaced by 90° relative to one another.

Figure 13:
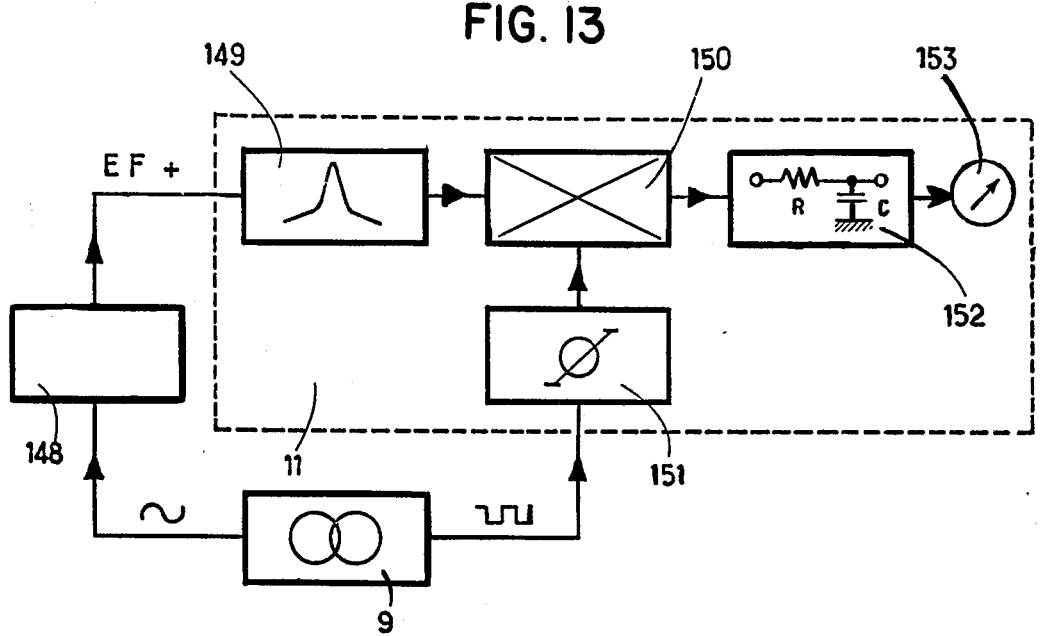
FIG. 13 is a block diagram showing how a synchronous detector works.

The inductive probe 4 for measuring the current if attacks the amplifier/integrator 5 which attacks a selective amplifier 199 identical with that shown in FIG. 13 (reference 149). The output of this amplifier 199 is connected to two synchronous detectors 200 and 201 which are identical with the detector 150 shown in FIG. 13 and one of which 200 is controlled by the signal in quadrature with the reference, whilst the second 201 is controlled by the signal in phase with the reference, these two signals being delivered by the slave phase shifter 198. The output of the detector 200 is connected to the control input of the phase shifter 198.

The terminals of the cell 1-2 are connected to the input of the limiter 6 whose output is connected to the impedance adaptor/d.c.-a.c. separator 7. The output of 7 is connected to the input of a selective amplifier 202, identical with 149 in FIG. 13, whose output attacks the synchronous detector 203 controlled by the square signal in phase with the reference delivered by the slave phase shifter 198.

Figure 21:
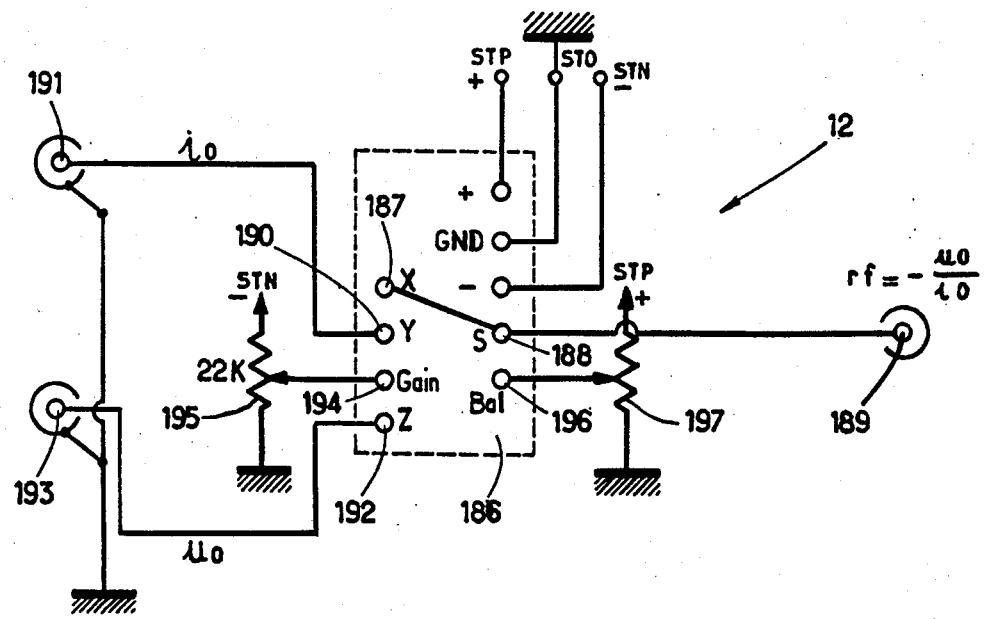
FIG. 21 is a circuit diagram of a dividing operator.

The respective outputs of the synchronous detectors 201 and 203 are connected to the inputs of a dividing operator 204 similar to that shown in FIG. 21, except that it has a third input connected to a stage 205 for processing a corrective factor K explained hereinafter. The output of the dividing operator 204 is connected to a reader 206 showing the resistance value R of the cell.

A resistance 207 of very low value is connected in series with the cell after the pole 51. This resistance, which is common to all the cells of an installation, forms a shunt which enables the direct current I flowing through the cell to be measured. The terminals of this resistance are connected to the input of a galvanically insulated measuring amplifier 208 identical with that shown in FIG. 20 except that it has a differential input. The output of this amplifier is connected to the "intensity" input of a multiplying operator 209 of which the "resistance" input is connected to the output of the dividing operator 204. The output of the multiplier 209 is connected to the input of a subtracting operator 210 of which the output is connected to a measuring apparatus 211 showing the counterelectromotive force of the cell.

The current I may also be measured by means of an inductive probe. In this case, the galvanic insulation is no longer necessary. The operation of the arrangement shown in FIG. 22 will now be described.

The square reference signal at the frequency f coming from the low-frequency generator 9 by way of the galvanically insulated reference amplifier 10, is applied to the input of the slave phase shifter 198 which delivers two square signals phase-displaced by 90° relative to one another.

The signal if coming from the inductive probe 4 is amplified in the amplifier 5, filtered in the selective amplifier 199 and then measured by the two synchronous detectors 200 and 201, of which the first 200 is controlled by the signal in quadrature with the reference determined by the 90° output of the slave phase shifter 198, whilst the second 201 is controlled by the signal in phase with the reference determined by the 0° output of the slave phase shifter 198. The essentially variable phase angle $\phi$ which exists between the current if flowing through the cell and the reference signal produces, at the output of the synchronous detector 200, a signal: io sin O, where io is the modulus of if. This synchronous detector 200 functions as a zero detector and attacks the control input of the phase shifter 198 by negative feedback. Thus any phase error between the reference signal and the modulus of if is collected by the action of the detector 200 on the slave phase shifter 198. The 0° output of the phase shifter 198 is thus in phase with the modulus of if so that the synchronous detector 201 measures io.

The voltage V taken from the terminals of the cell is limited by the limiter 6 and then applied to the impedance adaptor/d.c.-a.c. separator 7 which separates the d.c. component U from the a.c. component uf. The a.c. component passes through the selective amplifier 202 and is then measured by the synchronous detector 203 of which the reference is delivered from the 0° output of the slave phase shifter 198, so that it is in phase with if. The output of this detector 203 thus gives the term: Uo cos$\phi$ where ($\phi$) is the phase angle Uf relative to if.

The dividing operator 204 carries out the operation $$Rf = \frac{Uo \cos \phi}{io}$$

The voltage removed at the terminals of the shunt 207, which is the image of I, passes through the galvanically insulated measuring amplifier 208 and is then applied to the multiplying operator 209 which, on the other hand, receives the signal Rf. Accordingly, it processes Rf.I which, in turn, is applied to the subtracting operator 210 which, on the other hand, receives the signal U emitted by the amplifier/separator 7, cf. FIG. 7, tap 110 and which, as a result, gives the value U - Rfi, i.e., Ef which is shown by the apparatus 211.

If the frequency of the generator 9 could be made to incline towards zero, Rf would incline towards R and Ef towards E. Unfortunately, although it is possible on a laboratory scale to descend to frequencies of the order of 0.1 to 0.2 c/s, this is not possible on an industrial scale. Accordingly, it is only possible to drop to a frequency of a few cycles per second and to extrapolate to the zero frequency the curve giving Rf and Ef as a function of the frequency.

In practice, it is sufficient to use a simplified empirical method. With a knowledge of Rf at low frequency, it is possible to deduce R and the factor $$K = \frac{R}{Rf}$$

as a function of the frequency. By measuring at a single frequency f correctly selected, it is possible to obtaian Rf and, by multiplying by the coefficient K, to arrive at the result R = K Rf.

The value of K is thus entered in the processor 205 which introduces an image of K into the dividing operator 204. This operator then works out: KRf, i.e., R. it follows that the subtracting operator 210 works out E = U-RI.

Figure 23:
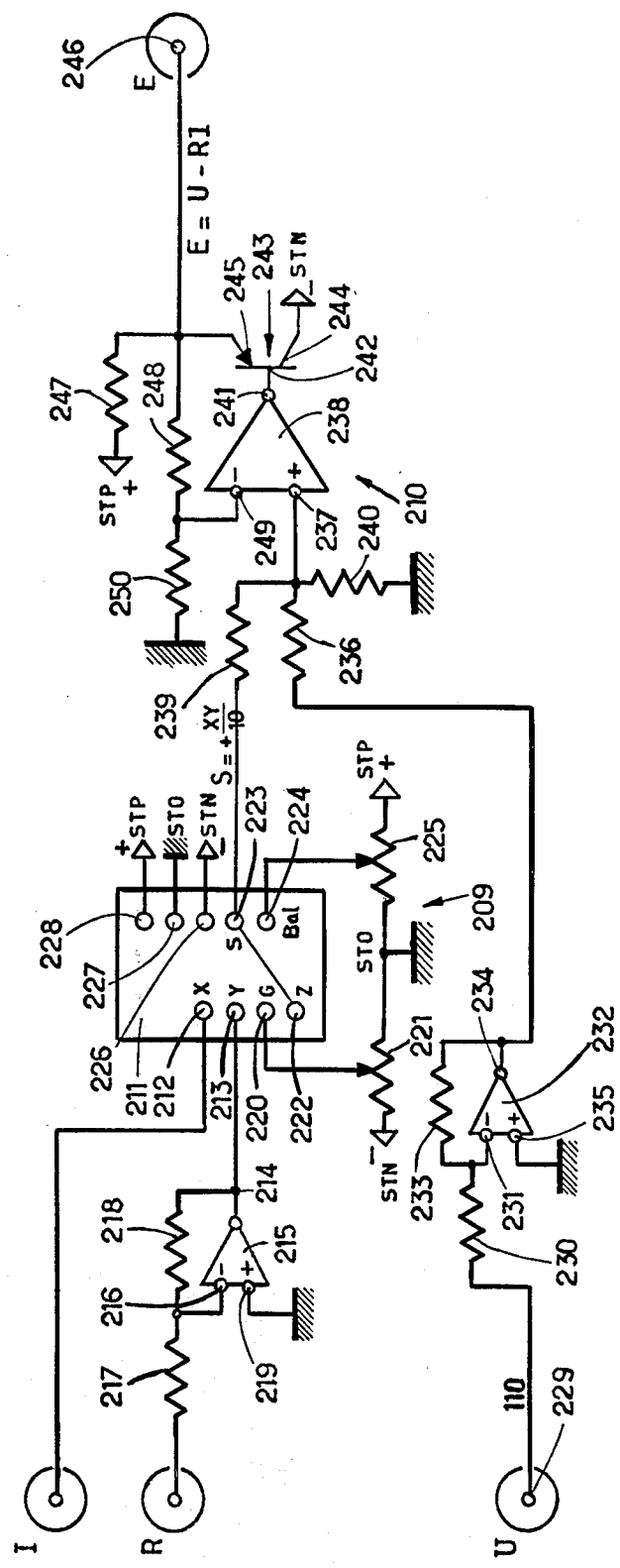
FIG. 23 is a circuit diagram of a multiplying operator followed by a subtracting operator.

All the elements of this apparatus described above in reference to FIGS. 1 to 21 are commercially available, except for the multiplying operator 209 and the subtracting operator 210. The circuitry of these two elements is shown in FIG. 23.

A multiplying module 211 has its first input 212, marked x, connected to the output of the galvanically insulated measuring amplifier 208 which gives I, and its second input 213, marked y, connected to the output 214 of an impedance-adapting stage 215 of which the negative input 216 is connected on the one hand by a resistance 217 to the output of the dividing operator 204 which gives R and on the other hand by a resistance 218, equal to the resistance 217, to the output 214. The positive input 219 of the stage 215 is connected to earth. The third input 220, marked "gain", of the module 211 is connected to the slide of a potentiometer 221 connected to the negative terminals of the voltage source ST, i.e., between the terminals STO and STN, whilst the fourth input 222 is connected to the output 223, thus giving the module its multiplying character. An auxiliary output 224, marked "Bal", is connected to the slide of a potentiometer 225 connected between STO and STP of the voltage source ST. The three feed connections 226, 227 and 228 are respectively connected to STN, STO and STP of the source ST.

Figure 7:
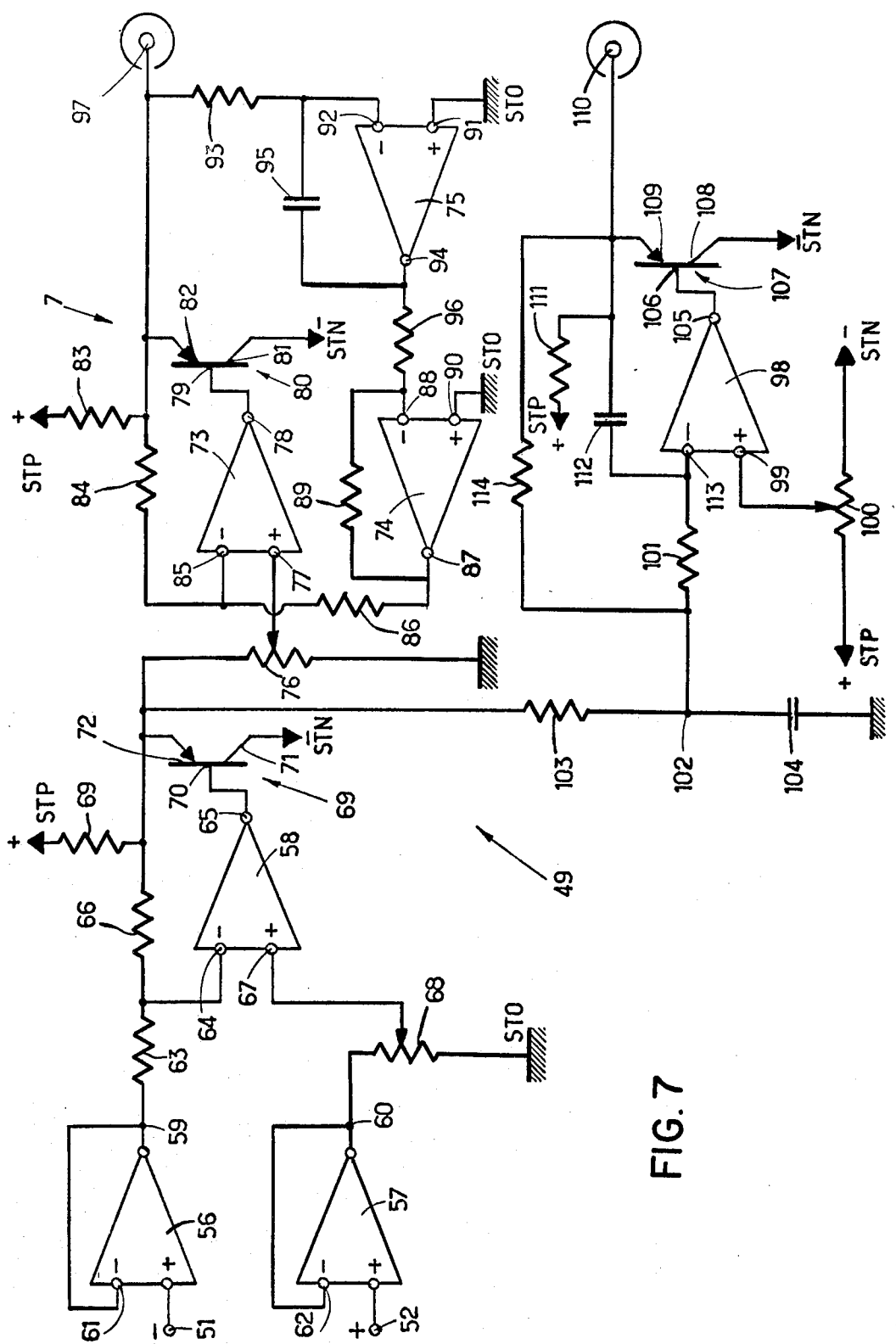
FIG. 7 is a circuit diagram of an amplifier which adapts impedance and separates alternating current.

The input U, which is denoted by the reference 229, is connected to the output 110 of the separator 7 shown in FIG. 7. It is connected by a resistance 230 to the negative input 231 of a stage 232 which, on the other hand, is connected by a resistance 233, equal to 230, to the output 234 of the stage. The positive input 235 of the stage is connected to earth.

The output 234 of the stage 232 is connected by a resistance 236 to the positive input 237 of a stage 238. This input is also connected, on the one hand by a resistance 239, to the output 233 of the module 211, and, on the other hand by a resistance 240, to earth. The three resistances 236, 239 and 240 are equal. U and RI must have the same coefficient of proportionality. The output 241 of the stage 238 is connected to the base 242 of an impedance adaptor/power amplifier transistor 243 whose collector 244 is connected to the negative pole STN of the d.c. voltage source ST, whilst its emitter 245 is connected to the output 246 giving E and, on the one hand by a resistance 247, to the positive pole STP of the source in ST, and, on the other hand by a resistance 248, to the negative input 249 of the stage 238, which is itself connected to earth, i.e, to the centre point STO of the source ST, by a resistance 250.

The operation of the multiplying and subtracting operators is obvious. The module 211 receives a signal I at 212 and at 213, a signal R under a low impedance determined by the stage 215. Since the input Z is connected to the output S, the module functions as a multiplier and, at its output 223, releases a signal proportional to XY, i.e., to RI. This signal U, adapted in impedance by the stage 232, is added to the signal RI at the input 237 of the stage 238, and transmitted to the output 246 under low impedance and high power by the transistor 243.

Figure 12:
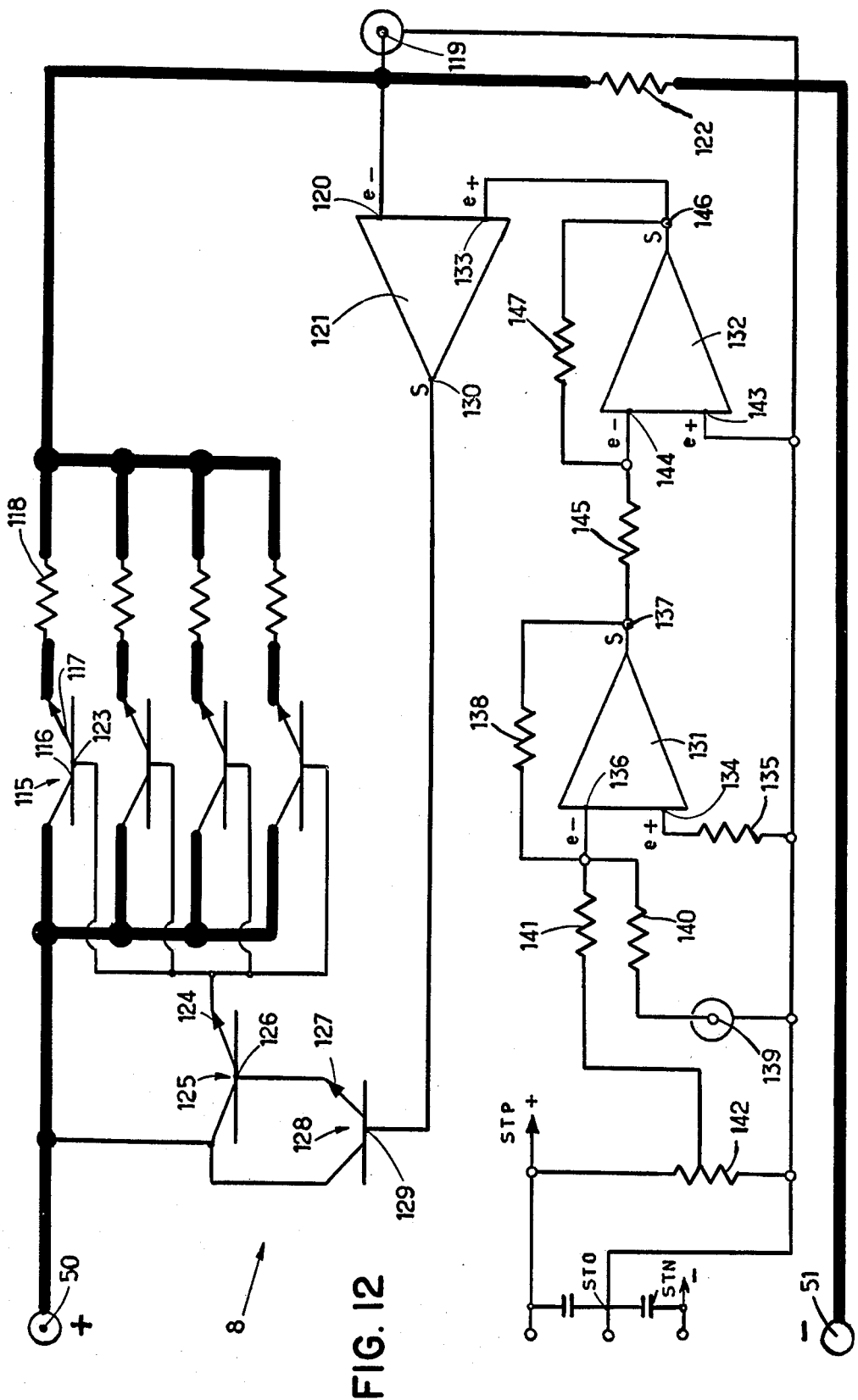
FIG. 12 is the complete circuit diagram of one exemplary converter.

In practice, all the stages of the apparatus consist of 2301 A integrated circuits, except for the stages: 28 FIG. 4, which is of the 8018 type, 121 FIG. 12, which is of the 1322 type, 173 and 182 FIG. 20, which are of the AD 301 AH type.

The Zener diodes 54 and 55 in FIG. 6 are of the 207 Z4 type for a variable resistance 53 of 110 ohms. The transistors 69, 80 and 107 in FIG. 7 are of the 2 N 2905 type. In FIG. 12, the transistors 115 and 125 are of the 2 N 3055 type for resistances 118 equal to 1 ohm and a shunt 122 of 0.01 ohm, the transistors 115 being cooled by the forced circulation of air. Finally, the transistor 128 is a 2 N 2219. In FIG. 20, the transistor 154 is a 2 N 3053 whilst, in FIG. 23, the transistor 243 is a 2 N 2905, the assembly formed by the diodes 164, 165 and the transistor 167 being commercially available under the reference 5082 – 4350. The multiplying-dividing circuits 186 in FIG. 21 and 211 in FIG. 23 are both of the 107C type.

The value of R obtained may be used to control an automatic system for controlling the anodic distance of the cell. A simultaneous increase in the values of R and E may be used to release the supply of alumina to the cell.

The method and apparatus according to the invention may be used for determining the resistance of any electrolysis cell, more especially electrolysis cells intended for the production of aluminium by the igneous electrolysis of alumina.

We claim:

1. A method for continuously determining the internal resistance (R) of an electrolysis cell from the voltage (U) at the terminals of the cell and from the current (I) flowing through the cell, a weak alternating current (if) of frequency (f) being superimposed upon the direct current (I) used for electrolysis, wherein the active part (rf) of the impedance which the cell offers to this alternating current is determined; followed by extrapolation to zero frequency of the function giving the active part (rf) of the impedance as a function of the frequency (f), this active value (rf) thus inclining towards the internal resistance (R) of the cell.

2. A method as claimed in claim 1 using synchronous detection, wherein the alternating current (if) is taken by induction from a bar feeding the cell, the signal obtained is brought back into phase with the alternating current (if), after which it is measured by synchronous detection from a reference formed by a voltage of frequency (f), a voltage (V) is tapped at the terminals, the a.c. component (uf) is separated from that voltage and measured by synchronous detection from the same reference voltage of frequency (f), and finally the modulus (uo) of (uf) is divided by the modulus (io) of (if)

to obtain the active component (rf) of the impedance of the cell, followed by extrapolation by making the frequency (f) tend towards zero so as to make the active component (rf) tend towards the internal resistance (R) of the cell.

3. A method as claimed in claim 1, wherein the phase of the reference signal of frequency (f) of the synchronous detections is synchronized with that of the a.c. component (if) of the current flowing through the cell.

4. A method as claimed in claim 1, wherein extrapolation to the zero frequency is carried out by tracing the curve representing the active component (rf) of the impedance of the cell as a function of the frequency (f), this curve is extrapolated to the zero frequency so as to obtain: r = rf(f=0), after which a frequency (f) is selected and the ratio (K) of the internal resistance (R) of the cell to the active component (rf) of its impedance at the frequency (f) selected is assumed to be constant, which enables the internal resistance (R) to be obtained by multiplying the active value (rf) of the impedance of the cell measured at the frequency (f) by the coefficient K (assumed to be constant).

5. An apparatus using the method claimed in claim 1 comprising synchronous detectors and a generator (9) of frequency (f) with a sinusoidal output and an in-phase square signal output, wherein the sinusoidal output of the generator (9) is connected to a current converter (8) connected between two points (50) and (51) on the feed bars (3) of the cell (1-2) on either side thereof, and superimposing a sinusoidal current (if) upon the direct current (1) flowing through the cell, the square signal output of the generator (9) is connected to the input of a galvanically insulated reference amplifier (10), said apparatus further comprising an inductive probe (4) for measuring the current (if) placed between the points (50) and (51) of the feed bars and attacking a first synchronous detector (11) whose reference input is connected to the output (176) of the galvanically insulated reference amplifier (10), an amplifier/a.c.-d.c. separator (7) whose inputs are connected to the poles (1) and (2) of the cell and whose output (97) giving the a.c. component (uf) of the voltage (U) at the poles of the cell is connected to the input of a second synchronous detector (11) whose reference input is also connected to the output (176) of the galvanically insulated reference amplifier (10), and a dividing operator (12) whose inputs are respectively connected to the outputs (Uof) and (iof) of the synchronous detectors (11) associated with (uf) and (if).

6. An apparatus as claimed in claim 5 of which the generator (9) of frequency (7) has only one sinusoidal output, wherein the input of the galvanically insulated reference amplifier (10) is connected to that sinusoidal output, its output being connected to the reference input of the synchronous detectors (11) through a device transforming the sinusoidal signal into a square signal.

7. An apparatus as claimed in claim 5 comprising a low-frequency generator (9) of frequency (f) with, on the one hand, a sinusoidal output connected to a current converter (8) connected between two points (50) and (51) on the feed bars (3) of the cell (1-2) on either side thereof, and on the other hand a square signal output connected to the input of a galvanically insulated reference amplifier (10), an inductive probe (4) placed between the points (50) and (51) of the feed bars and attacking, through an impedance adapter/integrator (5), a first synchronous detector (201), a separator amplifier (7) whose inputs are connected to the poles of the cell and whose output (97) giving the a.c. component of the voltage at the poles of the cell attacks a second synchronous detector (203), the outputs of the first and second synchronous detector (201) and (203) being respectively connected to the inputs (101) and (193) of a dividing operator (204) giving, at its output, the active component (rf) of the impedance of the cell at the frequency (f), wherein the output of the galvanically insulated amplifier (10) is connected to the input of a slave phase shifter (198) comprising a 0-phase output connected to the reference inputs of the first and second synchronous detectors (201) and (203) and a 90° output connected to the reference input of an auxiliary synchronous detector (200) attacked by the output of the impedance adapter/integrator (5) and of which the output is connected to the control input of the slave phase shifter (198) so that the reference signal of the first and second synchronous detectors (201) and (203) is synchronized with the a.c. component (if) of the current flowing through the cell.

8. An apparatus as claimed in claim 7, comprising a processor (205) processing a factor K whose output is connected to a multiplication input of the dividing operator (204) so that the product K.rf = R is obtained at the output of this operator.

9. An apparatus as claimed in claim 7 comprising a shunt (207) for measuring the intensity of the direct current (1) flowing through the cell connected in series in the feed bar (3) of the cell outside the points (50)-(51), of which the terminals are respectively connected to the inputs of a galvanically insulated measuring amplifier (208) with differential inputs, wherein the output (R) of the dividing operator (204) is connected to an input of a multiplying operator (209) whose other input is connected to the output of the galvanically insulated amplifier (208) and whose output (223) is connected to the input of a subtracting operator (210) whose second input is connected to the output (110) of the separator amplifier (7) giving the d.c. voltage (1) of the cell and whose output gives the counterelectromotive force of electrolysis E = U − RI.

10. An apparatus as claimed in claim 9 in which the intensity of the direct current 1 flowing through the cell is measured by an inductive probe, wherein the second input of the multiplying operator (209) is directly connected to this inductive probe.

11. An apparatus as claimed in claim 7 wherein the current converter (8) comprises at least one power transistor (115) in series with a shunt (122) connected in parallel with the points (50) and (51) on the feed bars (3) of the cell on either side thereof, the bases (123) of these transistors being connected to the output of an amplifier (121 - 125 - 128) with two differential inputs, of which one (120) is connected to the shunt (122), while the other is connected to the sinusoidal output of the generator (9) through an amplifier (131 - 132).

12. An apparatus as claimed in claim 5 wherein it is used in cells for the production of aluminum by the igneous electrolysis of alumina.

* * * * *

UNITED STATES PATENT OFFICE
CERTIFICATE OF CORRECTION

Patent No. 3,969,669      Dated  July 13, 1976

Inventor(s)  Thierry Brault; Jean-Claude Lacroix

It is certified that error appears in the above-identified patent and that said Letters Patent are hereby corrected as shown below:

Column 2, line 16, cancel "examination";

Column 6, line 24, after "intensity" insert --- (if) ---.

Signed and Sealed this

Nineteenth Day of October 1976

[SEAL]

Attest:

RUTH C. MASON
*Attesting Officer*

C. MARSHALL DANN
*Commissioner of Patents and Trademarks*